United States Patent [19]

Restle et al.

[11] Patent Number: 6,039,936
[45] Date of Patent: Mar. 21, 2000

[54] NANOEMULSION BASED ON NON-IONIC AND CATIONIC AMPHIPHILIC LIPIDS AND USES THEREOF

[75] Inventors: Serge Restle, Saint-Prix; Daniéle Cauwet-Martin, Paris, both of France

[73] Assignee: L'Oreal, France

[21] Appl. No.: 08/969,796

[22] Filed: Nov. 13, 1997

[30] Foreign Application Priority Data

Nov. 15, 1996 [FR] France ................................. 9613978
Mar. 18, 1997 [FR] France ................................. 9703281

[51] Int. Cl.[7] .......................................... A61K 7/06
[52] U.S. Cl. ..................... 424/70.1; 424/401; 424/70.11; 424/70.19; 424/70.27; 424/70.31; 514/937; 514/938
[58] Field of Search ................... 424/401, 70.1, 424/70.11, 70.19, 70.27, 70.31; 514/937, 938

[56] References Cited

U.S. PATENT DOCUMENTS

| | | | |
|---|---|---|---|
| 4,559,226 | 12/1985 | Fogel et al. ............................. | 424/66 |
| 4,880,621 | 11/1989 | Grollier et al. ......................... | 424/74 |
| 5,246,693 | 9/1993 | Grollier et al. ......................... | 424/70 |
| 5,298,240 | 3/1994 | Schröder et al. ....................... | 424/70 |
| 5,585,104 | 12/1996 | Ha et al. ................................. | 424/401 |
| 5,753,241 | 5/1998 | Ribier et al. ........................... | 424/401 |

FOREIGN PATENT DOCUMENTS

| | | |
|---|---|---|
| 0 334 777 | 9/1989 | European Pat. Off. . |
| 0 433 131 | 6/1991 | European Pat. Off. . |
| 0 433 132 | 6/1991 | European Pat. Off. . |
| 2 730 932 | 8/1996 | France . |
| 1-293131 | 11/1989 | Japan . |

OTHER PUBLICATIONS

English language translation of JP1–293131.
English Language Derwent Abstract of EP 0 334 777.
English Language Derwent Abstract of EP 0 433 132.
English Language Derwent Abstract of FR 2 730 932.

*Primary Examiner*—Thurman K. Page
*Assistant Examiner*—Lakshmi Channavajjala
*Attorney, Agent, or Firm*—Finnegan, Henderson, Farabow, Garrett & Dunner, L.L.P.

[57] ABSTRACT

An oil-in-water emulsion, the oil globules of which have a mean size of less than 150 nm, comprising an amphiphilic lipid phase containing at least one non-ionic amphiphilic lipid which is liquid at an ambient temperature of less than 45° C. and at least one cationic amphiphilic lipid, and its uses in cosmetics or in dermopharmaceuticals.

16 Claims, No Drawings

NANOEMULSION BASED ON NON-IONIC AND CATIONIC AMPHIPHILIC LIPIDS AND USES THEREOF

The present invention is directed to an oil-in-water emulsion comprising oil globules which have a mean size of less than 150 nm and an amphiphilic lipid phase based on non-ionic amphiphilic lipids which are liquid at an ambient temperature of less than 45° C. and on cationic amphiphilic lipids, and to their use in topical applications, in particular in cosmetics and in dermopharmaceuticals.

Oil-in-water emulsions are well known in the field of cosmetics and of dermopharmaceuticals, in particular for the preparation of cosmetic products, such as lotions, tonics, serums or eaux de toilette (toilet waters).

However, the presence of high concentrations of vegetable, animal or mineral oils in compositions makes them difficult to formulate. This is because the compositions are generally unstable on storage and the cosmetic properties are unsatisfactory. In particular, the application of such compositions to the hair leads to a greasy feel and difficulty in rinsing. Moreover, hair subsequently dried is without body and has a heavy feel.

Nanoemulsions comprising an amphiphilic lipid phase composed of phospholipids, of a cationic lipid, of water and of a hydrophobic sunscreening agent are known in the state of the art. Such nanoemulsions are obtained by a high-pressure homogenization process. These emulsions exhibit the disadvantage of being unstable on storage at conventional storage temperatures, namely between 0 and 45° C. They result in yellow compositions and produce rancid smells which develop after a few days of storage. Moreover, these emulsions do not contribute good cosmetic properties. They are described in the review "DCI" of April 1996, pages 46–48.

The inventors have discovered, unexpectedly, new emulsions containing oil globules having a mean size of less than 150 nm and which are stable on storage between 0 and 45° C. after at least one month. The nanoemulsions in accordance with the invention are prepared at temperatures between 20 and 45° C. and are compatible with heat-sensitive active ingredients. They can contain large amounts of oil. They can, in particular, contain large amounts of fragrance and can improve their persistence. They also promote penetration of the active ingredients into the surface layers of the skin and the deposition of active ingredient on keratinous fibres, such as hair. Hair treated with these nanoemulsions is glossy without having a greasy feel or appearance, it disentangles easily and is softer and livelier.

A subject of the present invention is accordingly oil-in-water emulsions having oil globules with a mean size of less than 150 nm, characterized in that they comprise an amphiphilic lipid phase comprising at least one non-ionic amphiphilic lipid which is liquid at an ambient temperature of less than 45° C. and at least one cationic amphiphilic lipid and in that the ratio by weight of the amount of oil to the amount of amphiphilic lipid phase ranges from 2:1 to 10:1 and preferably from 3:1 to 6:1.

The non-ionic amphiphilic lipids of the invention are preferably chosen from silicone surfactants and esters of at least one polyol chosen from the group formed by polyethylene glycol containing from 1 to 60 ethylene oxide units, sorbitan, glycerol containing from 2 to 30 ethylene oxide units or polyglycerols containing from 2 to 15 glycerol units and of at least one fatty acid containing at least one saturated or unsaturated, linear or branched, $C_8$–$C_{22}$ alkyl chain. It is also possible to use mixtures of the above compounds.

The silicone surfactants which can be used according to the invention are silicone compounds containing at least one oxyethylenated —$OCH_2CH_2$— and/or oxypropylenated —$OCH_2CH_2CH_2$— chain. Mention may be made, as silicone surfactants which can be used according to the present invention, of those described in U.S. Pat. Nos. 5,364,633 and 5,411,744, the disclosures of which are specifically incorporated by reference herein.

The silicone surfactant used according to the present invention is preferably a compound of formula (I):

$$R_1\text{—Si}(CH_3)_2\text{—O—}[Si(CH_3)_2\text{—O}]_A\text{—}[Si(CH_3)(R_2)\text{—O}]_B\text{—Si}(CH_3)_2\text{—}R_3$$

in which:

$R_1$, $R_2$ and $R_3$, independently of one another, represent a $C_1$–$C_6$ alkyl radical or a —$(CH_2)_x$—$(OCH_2CH_2)_y$—$(OCH_2CH_2CH_2)_z$—$OR_4$ radical,; at least one $R_1$, $R_2$ or $R_3$ radical not being an alkyl radical; $R_4$ being a hydrogen, an alkyl radical or an acyl radical;

A is an integer ranging from 0 to 200;

B is an integer ranging from 0 to 50; provided that A and B are not simultaneously equal to zero;

x is an integer ranging from 1 to 6;

y is an integer ranging from 1 to 30; and z is an integer ranging from 0 to 5.

According to a preferred embodiment of the invention, in the compound of formula (I), the alkyl radical is a methyl radical, x is an integer ranging from 2 to 6 and y is an integer ranging from 4 to 30.

Mention may be made, as example of silicone surfactants of formula (I), of the compounds of formula (II):

$$(CH_3)_3SiO\text{—}[(CH_3)_2SiO]_A\text{—}(CH_3SiO)_B\text{—}Si(CH_3)_3 \quad (II)$$
$$\quad\quad\quad\quad\quad\quad\quad\quad\quad\quad | $$
$$\quad\quad\quad\quad\quad\quad\quad\quad (CH_2)_2\text{—}(OCH_2CH_2)_y\text{—}OH$$

in which A is an integer ranging from 20 to 105, B is an integer ranging from 2 to 10 and y is an integer ranging from 10 to 20.

Mention may also be made, as an example of silicone surfactants of formula (I), of the compounds of formula (III):

$$HO\text{—}(OCH_2CH_2)_y\text{—}(CH_2)_3\text{—}[(CH_3)_2SiO]_{A'}\text{—}(CH_2)_3\text{—}(OCH_2CH_2)_y\text{—}OH \quad (III)$$

in which A' and y are integers ranging from 10 to 20.

It is possible to use, as compounds of the invention, those sold by the company Dow Corning under the names DC 5329, DC 7439-146, DC 2-5695 and Q4-3667. The compounds DC 5329, DC 7439-146 and DC 2-5695 are compounds of formula (II) where, respectively, A is 22, B is 2 and y is 12; A is 103, B is 10 and y is 12; and A is 27, B is 3 and y is 12.

The compound Q4-3667 is a compound of formula (III) where A is 15 and y is 13.

Mention may more preferably be made, among non-ionic amphiphilic lipids, by way of example, of:

polyethylene glycol isostearate, the glycol having a molecular weight of 400, diglyceryl isostearate, polyglycerol laurate containing 10 glycerol units, sorbitan oleate, sorbitan isostearate, and α-butylglucoside cocoate or α-butylglucoside caprate.

The cationic amphiphilic lipids used in the nanoemulsions of the invention are preferably chosen from the group formed by quaternary ammonium salts, fatty amines and salts thereof.

The quaternary ammonium salts are, for example:

those which exhibit the following general formula (IV):

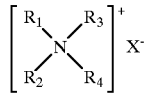

(IV)

in which the $R_1$ to $R_4$ radicals, which can be identical or different, represent a linear or branched aliphatic radical containing from 1 to 30 carbon atoms, or an aromatic radical, such as aryl, for example, phenyl or benzyl, or alkylaryl, for example, $(C_1–C_6)$ alkylaryl. The aliphatic radicals can contain heteroatoms, such as, in particular, oxygen, nitrogen, sulphur or halogens. The aliphatic radicals are, for example, chosen from alkyl, alkoxy, polyoxy $(C_2–C_6)$alkylene, alkylamide, $(C_{12}–C_{22})$- alkylamido $(C_2–C_6)$alkyl, $(C_{12}–C_{22})$alkyl acetate or hydroxyalkyl radicals containing approximately from 1 to 30 carbon atoms; X is an anion chosen from the halides, phosphates, acetates, lactates, $(C_2–C_6)$alkyl sulphates, or alkyl- or alkylarylsulphonates, imidazolinium quaternary ammonium salts, such as, for example, that of following formula (V):

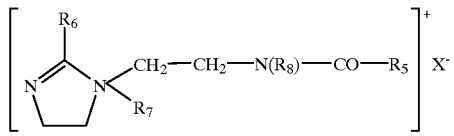

(V)

in which $R_5$ represents an alkenyl or alkyl radical containing from 8 to 30 carbon atoms, for example derivatives of tallow fatty acids, $R_6$ represents a hydrogen atom, a $C_1–C_4$ alkyl radical or an alkenyl or alkyl radical containing from 8 to 30 carbon atoms, $R_7$ represents a $C_1–C_4$ alkyl radical, $R_8$ represents a hydrogen atom or a $C_1–C_4$ alkyl radical and X is an anion chosen from halides, phosphates, acetates, lactates, alkyl sulphates, or alkyl- or alkylarylsulphonates. $R_5$ and $R_6$ preferably denote a mixture of alkenyl or alkyl radicals containing from 12 to 21 carbon atoms, for example, derivatives of tallow fatty acids, $R_7$ preferably denotes methyl and $R_8$ preferably denotes hydrogen. Such a product is, for example, sold under the name "Rewoquat W 75" by the company Rewo, quaternary diammonium salts of formula (VI):

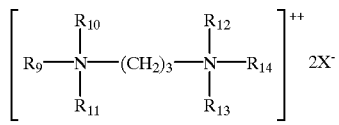

(VI)

in which $R_9$ denotes an aliphatic radical containing approximately from 16 to 30 carbon atoms, $R_{10}$, $R_{11}$, $R_{12}$, $R_{13}$ and $R_{14}$, which are identical or different, are chosen from hydrogen or an alkyl radical containing from 1 to 4 carbon atoms and X is an anion chosen from the group of halides, acetates, phosphates, nitrates and methyl sulphates. Such quaternary diammonium salts comprise in particular propanetallowdiammonium dichloride, quaternary ammonium salts containing at least one ester functional group.

The quaternary ammonium salts containing at least one ester functional group which can be used according to the invention are, for example, those of formula (VII):

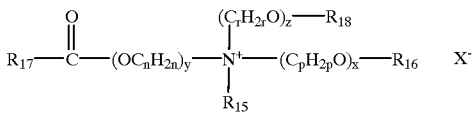

(VII)

in which:

$R_{15}$ is chosen from $C_1–C_6$ alkyl radicals and $C_1–C_6$ hydroxyalkyl or dihydroxyalkyl radicals;

$R_{16}$ is chosen from:

the $R_{19}$

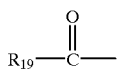

radical, saturated or unsaturated, linear or branched, $C_1–C_{22}$ hydrocarbon radicals $R_{20}$, the hydrogen atom, $R_{18}$ is chosen from:

the $R_{21}$

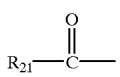

radical, saturated or unsaturated, linear or branched, $C_1–C_6$ hydrocarbon radicals $R_{22}$, the hydrogen atom, $R_{17}$, $R_{19}$ and $R_{21}$, which are identical or different, are chosen from saturated or unsaturated, linear or branched, $C_7–C_{21}$ hydrocarbon radicals;

n, p and r, which are identical or different, are integers having values from 2 to 6;

y is an integer having a value from 1 to 10;

x and z, which are identical or different, are integers having values from 0 to 10;

$X^−$ is an organic or inorganic, simple or complex anion;

with the proviso that the sum x+y+z has a value from 1 to 15, that when x has a value of 0, then $R_{16}$ denotes $R_{20}$, and that when z has a value of 0, then $R_{18}$ denotes $R_{22}$.

The $R_{15}$ alkyl radicals can be linear or branched and are more preferably linear.

$R_{15}$ preferably denotes a methyl, ethyl, hydroxyethyl or dihydroxypropyl radical and more preferably a methyl or ethyl radical.

The sum x+y+z advantageously has a value from 1 to 10.

When $R_{16}$ is an $R_{20}$ hydrocarbon radical, it can be long and have from 12 to 22 carbon atoms or it can be short and have from 1 to 3 carbon atoms.

When $R_{18}$ is an $R_{22}$ hydrocarbon radical, it preferably has 1 to 3 carbon atoms.

$R_{17}$, $R_{19}$ and $R_{21}$, which are identical or different, are advantageously chosen from saturated or unsaturated, linear or branched, $C_{11}$–$C_{21}$ hydrocarbon radicals and more particularly from saturated or unsaturated, linear or branched, $C_{11}$–$C_{21}$ alkyl and alkenyl radicals.

Preferably, x and z, which are identical or different, have the value 0 or 1.

Advantageously, y is equal to 1.

Preferably, n, p and r, which are identical or different, have a value of 2 or 3 and, more preferably still, are equal to 2.

The anion is preferably a halide (chloride, bromide or iodide) or an alkyl sulphate, more particularly methyl sulphate. However, it is possible to use methanesulphonate, phosphate, nitrate, tosylate, an anion derived from organic acid, such as acetate or lactate, or any other anion compatible with ammonium containing an ester functional group.

The $X^-$ anion is more particularly still chloride or methyl sulphate.

Use is more preferably made of the ammonium salts of formula (VII) in which:

$R_{15}$ denotes a methyl or ethyl radical, x and y are equal to 1;

z is equal to 0 or 1;

n, p and r are equal to 2;

$R_{16}$ is chosen from:
the $R_{19}$

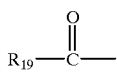

radical;
methyl, ethyl or $C_{14}$–$C_{22}$ hydrocarbon radicals
the hydrogen atom;

$R_{18}$ is chosen from:
the $R_{21}$

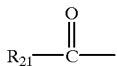

radical;
the hydrogen atom;

$R_{17}$, $R_{19}$ and $R_{21}$, which are identical or different, chosen from saturated or unsaturated, linear or branched, $C_{13}$–$C_{17}$ hydrocarbon radicals and preferably from saturated or unsaturated, linear or branched, $C_{13}$–$C_{17}$ alkyl and alkenyl radicals.

The hydrocarbon radicals are preferably linear.

Mention may be made, for example, of the compounds of formula (VII), such as diacyloxyethyl-dimethylammonium, diacyloxyethyl(hydroxyethyl)-methylammonium, monoacyloxyethyl(dihydroxyethyl)-methylammonium, triacyloxyethyl(methyl)ammonium or monoacyloxyethyl (hydroxyethyl)-dimethylammonium salts (chloride or methyl sulphate, in particular) and mixtures thereof. The acyl radicals preferably have 14 to 18 carbon atoms and more particularly originate from a vegetable oil, such as palm oil or sunflower oil. When the compound contains several acyl radicals, the latter can be identical or different.

These products are obtained, for example, by direct esterification of triethanolamine, of triisopropanolamine, of alkyldiethanolamine or of alkyldiisopropanolamine, which are optionally oxyalkylenated, with fatty acids or mixtures of fatty acids of vegetable or animal origin or by transesterification of their methyl esters. This esterification is followed by a quaternization using an alkylating agent, such as an alkyl (preferably methyl or ethyl) halide, a dialkyl (preferably methyl or ethyl) sulphate, methyl methanesulphonate, methyl para-toluenesulphonate, or glycol or glycerol chlorohydrin.

Such compounds are, for example, sold under the names Dehyquart by the company Henkel, Stepanquat by the company Stepan, Noxamium by the company Ceca or Rewoquat WE 18 by the company Rewo-Witco.

The composition according to the invention preferably contains a mixture of quaternary ammonium mono-, di- and triester salts, with a majority by weight of diester salts.

Use may be made of a mixture of ammonium salts of, for example, the mixture containing 15 to 30% by weight of acyloxyethyl(dihydroxyethyl)methyl-ammonium methyl sulphate, 45 to 60% of diacyloxyethyl-(hydroxyethyl) methylammonium methyl sulphate and 15 to 30% of triacyloxyethyl(methyl)ammonium methyl sulphate, the acyl radicals having from 14 to 18 carbon atoms and originating from optionally partially hydrogenated palm oil.

It is also possible to use the ammonium salts containing at least one ester functional group described in U.S. Pat. Nos. 4,874,554 and 4,137,180, the disclosures of which are specifically incorporated by reference herein.

Preference is given, among the quaternary ammonium salts of formula (IV), to, on the one hand, tetraalkylammonium chlorides, such as, for example, dialkyldimethylammonium or alkyltrimethylammonium chlorides in which the alkyl radical contains approximately from 12 to 22 carbon atoms, in particular behenyltrimethylammonium, distearyldimethylammonium, cetyltrimethylammonium and benzyldimethylstearyl-ammonium chlorides, or alternatively, on the other hand, stearamidopropyldimethyl (myristyl acetate)-ammonium chloride sold under the name "Ceraphyl 70" by the company Van Dyk.

According to the invention, behenyltrimethyl-ammonium chloride is the most particularly preferred quaternary ammonium salt.

The cationic amphiphilic lipids are present in the nanoemulsions of the invention preferably in concentrations ranging from 1 to 60% by weight and more particularly from 10 to 50% by weight with respect to the total weight of the amphiphilic lipid phase.

The cationic amphiphilic lipids are present in the nanoemulsions of the invention preferably in concentrations ranging from 0.1 to 10% by weight with respect to the total weight of the nanoemulsion.

The nanoemulsions in accordance with the invention contain an amount of oil ranging preferably from 5 to 40% by weight with respect to the total weight of the emulsion and more particularly from 8 to 30% by weight.

The oils which can be used in the emulsions of the invention are preferably chosen from the group formed by:

animal or vegetable oils formed by esters of fatty acids and of polyols, in particular liquid triglycerides, for example sunflower, maize, soybean, avocado, jojoba, gourd, grape seed, sesame and hazelnut oils, fish oils or glycerol tricaprocaprylate, or vegetable or animal oils of formula $R_9COOR_{10}$, in which $R_9$ represents the residue of a higher fatty acid containing from 7 to 29 carbon atoms and $R_{10}$ represents a linear or branched hydrocarbon chain containing from 3 to 30 carbon atoms, in particular alkyl or alkenyl, for example Purcellin oil or liquid jojoba wax;

natural or synthetic essential oils, such as, for example, eucalyptus, lavandin, lavender, vetiver, litsea cubeba, lemon, santal, rosemary, camomile, savory, nutmeg, cinnamon, hyssop, caraway, orange, geraniol, cade and bergamot oils;

hydrocarbons, such as hexadecane and liquid paraffin;

halocarbons, in particular fluorocarbons, such as fluoroamines, for example perfluorotributylamine, fluorinated hydrocarbons, for example perfluorodecahydronaphthalene, fluoroesters and fluoroethers;

esters of an inorganic acid and of an alcohol;

ethers and polyethers;

silicones as a mixture with at least one of the oils defined above, for example decamethylcyclopentasiloxane or dodecamethylcyclohexasiloxane.

The emulsions in accordance with the present invention can contain additives for improving, if necessary, the transparency of the formulation.

These additives are preferably chosen from the group formed by:

lower $C_1$–$C_8$ alcohols, such as ethanol;

glycols, such as glycerol, propylene glycol, 1,3-butylene glycol, dipropylene glycol or polyethylene glycols containing from 4 to 16 ethylene oxide units and preferably from 8 to 12.

The additives, such as those mentioned above, are present in the emulsions of the invention in concentrations preferably ranging from 1 to 30% by weight with respect to the total weight of the emulsion.

In addition, the use of the alcohols as defined above at concentrations greater than or equal to 5% by weight and preferably greater than 15% makes it possible to obtain preservative-free emulsions.

The emulsions of the invention can contain water-soluble or fat-soluble active ingredients having a cosmetic or dermopharmaceutical activity. The fat-soluble active ingredients are present in the oil globules of the emulsion, whereas the water-soluble active ingredients are in the aqueous phase of the emulsion. Mention may be made, as examples of active ingredients, of vitamins, such as vitamin E and its derivatives, provitamins, such as panthenol, humectants, silicone or non-silicone sunscreening agents, surface-active agents, preserving agents, sequestrants, softeners, fragrances, dyes, viscosity-modifying agents, foam-modifying agents, foam stabilizers, pearlescent agents, pigments, moisturizing agents, antidandruff agents, antiseborrhoeic agents, proteins, silicones, ceramides, pseudoceramides, fatty acids containing linear or branched $C_{16}$–$C_{40}$ chains, such as 18-methyleicosanoic acid, thickeners, plasticizers, hydroxy acids, electrolytes and polymers, in particular cationic polymers.

Mention may be made, among the thickeners which can be used, of cellulose derivatives, such as hydroxymethylpropylcellulose, fatty alcohols, such as stearyl, cetyl and behenyl alcohols, derivatives of algae, such as satiagum, natural gums, such as gum tragacanth, and synthetic polymers, such as the mixtures of polycarboxyvinyl acids sold under the name Carbopol by the company Goodrich and the mixture of Na acrylate/acrylamide copolymers sold under the name Hostacerin PN 73 by the company Hoechst.

The oil globules of the emulsions of the invention preferably have a mean size ranging from 30 to 150 nm, more preferably from 40 to 100 nm and more preferably still from 50 to 80 nm.

The nanoemulsions of the invention can be obtained by a process, characterized in that the aqueous phase and the oily phase are mixed, with vigorous agitation, at an ambient temperature of less than 45° C. and in that a high-pressure homogenization is then carried out at a pressure greater than $10^8$ Pa, and preferably ranging from $12 \times 10^7$ to $18 \times 10^7$ Pa. Such a process makes it possible to produce, at ambient temperature, nanoemulsions which are compatible with heat-sensitive active compounds and which can contain large amounts of oils and in particular fragrances which contain fatty substances, without denaturing them.

Another subject of the invention comprises a composition for topical use, such as a cosmetic or dermopharmaceutical composition, characterized in that it is composed of an emulsion as defined above or in that it comprises such an emulsion. The invention more particularly relates to hair compositions.

The compositions in accordance with the invention can be used for washing, cleaning and removing make up from keratinous substances, such as hair, skin, eyelashes, eyebrows, nails or mucous membranes.

The compositions of the invention can more particularly be provided in the form of shampoos, rinse-out or leave-in conditioners, or perming, hair-straightening, dyeing or bleaching compositions, or alternatively in the form of compositions to be applied before or after dyeing, bleaching, perming or hair straightening or alternatively between the two stages of a perming or hair-straightening operation.

The compositions can also be hair-setting lotions, blow-drying lotions or fixing (lacquer) and styling compositions, such as, for example, gels or foams. The lotions can be packaged in various forms, in particular in vaporizers or pump-action sprays or in aerosol containers, in order to provide for application of the composition in the vaporized form or in the foam form. Such packaging forms are indicated, for example, when it is desired to obtain a spray, a lacquer or a foam for fixing or treating the hair.

When the composition according to the invention is packaged in aerosol form for the purpose of obtaining a lacquer or an aerosol foam, it comprises at least one propellant which can be chosen from volatile hydrocarbons, such as n-butane, propane, isobutane, pentane, chlorinated and/or fluorinated hydrocarbons and their mixtures. It is also possible to use, as a propellant, carbon dioxide, nitrous oxide, dimethyl ether, nitrogen or compressed air.

Another subject of the invention is the use of the emulsions as defined above as a base for products for caring for and/or making up and/or removing make-up from the skin and/or the face and/or the scalp and/or the hair and/or the nails and/or the eyelashes and/or the eyebrows and/or the mucous membranes (for example the lips), such as lotions, serums, milks, creams or eaux de toilette.

Finally, the invention also relates to a non-therapeutic process for caring for the skin, hair, eyelashes, eyebrows, nails, mucous membranes or scalp, characterized in that an emulsion as defined above is applied to the skin, hair, eyelashes, eyebrows, nails, mucous membranes or scalp.

The following examples will enable the invention to be better understood without, however, having a limiting nature.

EXAMPLES

The following procedure was employed for Examples 1 and 4:

in a first phase A, the non-ionic and cationic amphiphilic lipids were homogenized with the oil and the lipophilic active ingredients and adjuvants at a temperature of approximately 45° C.;

in a second phase B, the hydrophilic active ingredients and adjuvants were dissolved at a temperature of 20 to 30° C.;

the phases A and B were then mixed using a propeller homogenizer and then homogenization was carried out using a high-pressure homogenizer of the Soavi-Niro type at a pressure of 1500 bars, with 7 passages, while maintaining the temperature of the product below approximately 35° C.

Example 1

Avocado oil nanoemulsion

| First phase: | |
| --- | --- |
| PEG-400 isostearate, sold by the company Unichema | 4.5% |
| Behenyltrimethylammonium chloride (cationic amphiphilic lipid) | 0.5% |
| Avocado oil | 20% |
| Non-denatured absolute ethanol | 15% |
| Second phase: | |
| Demineralized water | 54.7% |
| Glycerol | 5% |

An emulsion was obtained in which the size of the oil globules was approximately 63 nm.

Example 2

Leave-in hair care composition

| | |
| --- | --- |
| Mixture of polyacrylamide, of $C_{13}$–$C_{14}$ isoparaffin and of laureth-7, sold under the name Sepigel 305 by the company Seppic | 0.9 g |
| Nanoemulsion of Example 1 | 15 g |
| Preservative, fragrance | q.s. |
| HCl | q.s.  pH 6 |
| Water | q.s. for 100 g |

Hair treated with this composition was easy to disentangle and had a natural and non-greasy feel.

Example 3

Rinse-out conditioner

| | |
| --- | --- |
| Cetylstearyl alcohol | 4 g |
| Mixture of myristyl, cetyl and stearyl myristate/palmitate/stearate, sold under the name Synthetic Spermaceti by the company Laserson | 1 g |
| Nanoemulsion of Example 1 | 10 g |
| Behenyltrimethylammonium chloride | 3 g |
| Preservative, fragrance | q.s. |
| Water | q.s. for 100 g |

Hair treated with this composition was easy to disentangle, soft and glossy.

Example 4

Avocado oil nanoemulsion

| First phase: | |
| --- | --- |
| PEG-400 isostearate, sold by the company Unichema | 4.5% |
| Distearylethylhydroxyethylammonium methyl sulphate (cationic amphiphilic lipid) | 0.5% |
| Avocado oil | 20% |
| Non-denatured absolute ethanol | 15% |
| Second phase: | |
| Demineralized water | 54.7% |
| Glycerol | 5% |

A particularly fluid emulsion was obtained in which the size of the globules was of the order of 50 nm.

Example 5

Shampoo

| | | |
| --- | --- | --- |
| Sodium lauryl ether sulphate (70/30 $C_{12}$/$C_{14}$) containing 2.2 mol of ethylene oxide as an aqueous solution containing 28% of AM | 17 g AM | |
| Cocoylbetaine (Dehyton AB 30) | 2.5 g AM | |
| Nanoemulsion of Example 4 | 7.5 g | |
| Coconut oil monoisopropanolamide | 3 g | |
| Ethylene glycol distearate | 3 g | |
| Fragrance, preservative | q.s. | |
| NaOH | q.s. | pH 7.1 |
| Demineralized water | q.s. for 100 g | |

This composition according to the invention exhibited an excellent foaming power. Hair treated with this composition was easy to disentangle, soft and glossy.

We claim:

1. An oil-in-water emulsion, said emulsion comprising oil globules whose mean size is less than 150 nm and an amphiphilic lipid phase, said amphiphilic lipid phase comprising at least one non-ionic amphiphilic lipid which is liquid at an ambient temperature of less than 45° C. and at least one cationic amphiphilic lipid, the ratio by weight of the amount of oil to the amount of said amphiphilic lipid phase in said emulsion ranging from 2:1 to 10:1.

2. An emulsion according to claim 1, wherein said ratio by weight of the amount of oil to the amount of said amphiphilic lipid ranges from 3:1 to 6:1.

3. An emulsion according to claim 1, wherein said at least one non-ionic amphiphilic lipid is (a) an ester of at least one polyol, said ester being a polyethylene glycol containing from 1 to 60 ethylene oxide units, sorbitan, glycerol containing from 2 to 30 ethylene oxide units, polyglycerol containing from 2 to 15 glycerol units, or a fatty acid containing at least one saturated or unsaturated, linear or branched, $C_8$–$C_{22}$ alkyl chain, or mixture thereof, or (b) a silicone surfactant.

4. An emulsion according to claim 1, wherein said at least one cationic amphiphilic lipid is a quaternary ammonium salt or a fatty amine.

5. An emulsion according to claim 4, wherein said quaternary ammonium salt is a:

quaternary ammonium salt of the formula

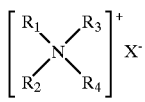

wherein the $R_1$ to $R_4$ radicals, which can be identical or different, represent a linear or branched aliphatic radical containing from 1 to 30 carbon atoms or an aromatic radical, and X is an anion selected from halides, phosphates, acetates, lactates, $(C_2-C_6)$alkyl sulphates, and alkyl- or alkylarylsulphonates, imidazolinium quaternary ammonium salt, quaternary diammonium salt of formula

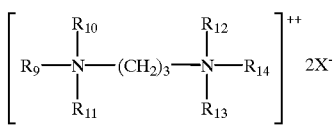

wherein $R_9$ denotes an aliphatic radical containing approximately from 16 to 30 carbon atoms, $R_{10}$, $R_{11}$, $R_{12}$, $R_{13}$ and $R_{14}$, which can be identical or different, are hydrogen or an alkyl radical containing from 1 to 4 carbon atoms, and X is an anion selected from halides, acetates, phosphates, nitrates and methyl sulphates, or quaternary ammonium salt containing at least one ester functional group.

6. An emulsion according to claim 5, wherein said aromatic radical is an aryl or alkylaryl.

7. An emulsion according to claim 1, wherein said at least one cationic amphiphilic lipid is present in a concentration ranging from 1 to 60% by weight with respect to the total weight of the amphiphilic lipid phase.

8. An emulsion according to claim 7, wherein said concentration ranges from 10 to 50% by weight with respect to the total weight of the amphiphilic lipid phase.

9. An emulsion according to claim 1, wherein the amount of oil present ranges from 5 to 40% by weight with respect to the total weight of the emulsion.

10. An emulsion according to claim 1, wherein the oil is selected from:

animal or vegetable oils formed by esters of fatty acids and of polyols;

animal or vegetable oils having the formula $R_9COOR_{10}$, wherein $R_9$ represents the residue of a higher fatty acid containing from 7 to 29 carbon atoms and $R_{10}$ represents a linear or branched hydrocarbon chain containing from 3 to 30 carbon atoms;

natural or synthetic essential oils;

hydrocarbons;

halocarbons;

esters of an inorganic acid and of an alcohol;

ethers and polyethers; and a mixture of at least one silicone with at least one of said animal or vegetable oils recited above.

11. An emulsion according to claim 1, wherein said emulsion further comprises a water-soluble or fat-soluble cosmetic or dermopharmaceutical active ingredient.

12. A composition for topical use, said composition comprising an oil-in-water emulsion according to claim 1.

13. A process for caring for, washing, making up and/or removing make-up from the body, face, mucous membranes, scalp, hair, nails, eyelashes and/or eyebrows, said process comprising applying an oil-in-water emulsion according to claim 1 to said body, face, mucous membranes, scalp, hair, nails, eyelashes and/or eyebrows.

14. A process for the non-therapeutic treatment of the skin, hair, mucous membranes, nails, eyelashes, eyebrows and/or scalp, said process comprising applying an emulsion according to claim 1 to said skin, hair, mucous membranes, nails, eyelashes, eyebrows and/or scalp.

15. A process for the preparation of an emulsion according to claim 1, said process comprising mixing the aqueous phase and the oily phase with vigorous agitation, at an ambient temperature of less than 45° C., and homogenizing said mixture at a pressure greater than $10^8$ Pa.

16. A process according to claim 15, wherein said pressure ranges from $12 \times 10^7$ to $18 \times 10^7$ Pa.

* * * * *